United States Patent

Sato et al.

Patent Number: 5,827,953
Date of Patent: Oct. 27, 1998

[54] METHOD OF TESTING HARDNESS IN REBOUND TYPE HARDNESS TESTER

[75] Inventors: Yasunori Sato; Junichi Arai; Yuichi Minami, all of Zama, Japan

[73] Assignee: Kabushiki Kaisha Akashi, Japan

[21] Appl. No.: 45,444

[22] Filed: Mar. 20, 1998

[30] Foreign Application Priority Data

Mar. 21, 1997 [JP] Japan .................................. 9-087534

[51] Int. Cl.$^6$ ...................................................... G01N 3/30
[52] U.S. Cl. .......................................................... 73/79
[58] Field of Search .................................................. 73/79

[56] References Cited

U.S. PATENT DOCUMENTS 2,654,244 10/1953 Braid ............................................ 73/79
3,879,982 4/1975 Schmidt ....................................... 73/79

Primary Examiner—Robert Raevis
Attorney, Agent, or Firm—Adams & Wilks

[57] ABSTRACT

An impacting velocity $v_1$ and a rebounding velocity $v_1'$ of the hammer at a second hammer velocity measurement point 12 a distance $x_1$ apart from a first hammer velocity measurement point 11 in the system of movement of the hammer are measured and the hardness H of the specimen is calculated in accordance with Equation 1, $$H = k \times \sqrt{\frac{v_1'^2 + 2\alpha(x_2 - x_1)}{v_1^2 + 2\alpha(x_2 - x_1)}} \quad [\text{Eq. 1}]$$

where $x_2$ denotes the distance between the first hammer velocity measurement point 11 and the specimen 2 and $\alpha$ denotes the acceleration acting on said hammer. Thereby, a hardness test in a rebound type hardness tester can be performed without measuring the velocities of the hammer immediately before impacting against the specimen and immediately after the impaction.

2 Claims, 1 Drawing Sheet 005,827,953

METHOD OF TESTING HARDNESS IN REBOUND TYPE HARDNESS TESTER

BACKGROUND OF THE INVENTION

1. Field of the Invention

The present invention relates to a method of testing hardness in a rebound type hardness tester in which a hammer is caused to impact a specimen and the harness of the specimen is measured from the ratio between hammer velocities before and after the impaction. More particularly it relates to a method of testing hardness in a rebound type hardness tester adapted to perform such hardness measurement without measuring hammer velocities immediately before and immediately after the impaction.

2. Description of the Related Art

Such an apparatus for measuring hardness of a specimen adapted to cause a hammer to impact the specimen and measure the hardness of the specimen in accordance with the ratio between the hammer velocity immediately before the impaction and the hammer velocity immediately after the impaction is called a rebound type hardness tester and put to practical use.

The principle of the measurement performed in the rebound type hardness tester will be described with reference to FIG. 2. Referring to FIG. 2, reference numeral 1 denotes a hammer and reference numeral 2 denotes a specimen. In the case where the hammer 1 impacts against the specimen 2 and rebounds from the same, let it be assumed that friction and air resistance against the hammer 1 while it is in motion can be neglected and no external force other than the gravitational force acts on the hammer 1 after it has been discharged. Hence, when the hammer 1 moves in the horizontal direction, the acceleration becomes zero and the hardness H of the specimen 2 is defined by the following Equation 3

$$H = k \times \frac{|v_2'|}{|v_2|} \quad [\text{Eq. 3}]$$

where $v_2$: hammer velocity immediately before impacting,
$v_2'$: hammer velocity immediately after impacting,
$k$: coefficient.

SUMMARY OF THE INVENTION

In an actual hardness test, however, it is difficult to accurately measure the velocity of the hammer when it impacts a specimen, i.e., the hammer velocity immediately before impacting $v_2$, and the velocity of the hammer immediately after it rebounded from the specimen, i.e., the hammer velocity immediately after impacting $v_2'$. Hence, there has been such a problem that there is no other way than to measure the impacting velocity and the rebounding velocity of the hammer at a position near the impacting point as approximate values and perform the hardness test on the basis of such approximate values.

The present invention was made to solve such a problem and accordingly it is an object of the invention to provide a method of measuring hardness in a rebound type hardness tester whereby the hardness test in the rebound type hardness tester can be performed without measuring the hammer velocity immediately before impacting $v_2$ and the hammer velocity immediately after impacting $v_2'$.

As the means for solving the above problem, the invention, in performing a hardness test in a rebound type hardness tester in which a hammer is caused to impact a specimen and a hardness test of the specimen is performed in accordance with the ratio of the velocities of the hammer before and after the impaction, comprises the step of calculating the hardness H of the specimen according to Equation 4 on the basis of a velocity $v_1$ in the impacting course and a velocity $v_1'$ in the rebounding course of the hammer at a second hammer velocity measurement point a distance $x_1$ closer to the specimen than a first hammer velocity measurement point, which is a distance $x_2$ apart from the specimen, along the passage for the hammer to go forward and backward, and the distance $x_1$, $$H = k \times \sqrt{\frac{v_1'^2 + 2\alpha(x_2 - x_1)}{v_1^2 + 2\alpha(x_2 - x_1)}} \quad [\text{Eq. 4}]$$

where $\alpha$ denotes the acceleration acting on the hammer.

Further, as the means for solving the above problem, the acceleration is calculating according to Equation 5 on the basis of a velocity $v_0$ of the hammer in the impacting course at the first hammer velocity measurement point, the velocity $v_1$ of the hammer in the impacting course at the second hammer velocity measurement point, and the distance $x_1$.

$$\alpha = \frac{v_1^2 - v_0^2}{2 x_1} \quad [\text{Eq. 5}]$$

According to the method of testing hardness of the invention in a rebound type hardness tester:

(1) since it is adapted such that the hammer velocities $v_1$ and $v_1'$ are measured at the hammer velocity measurement point at a certain height above the face of the specimen against which the hammer impacts, the hardness test using the rebound type hardness tester can be performed without measuring the hammer velocity immediately before impacting and immediately after impacting. Besides, since the velocities $v_1$ and $v_1'$ can be measured simply and very accurate measurement values can be obtained, the accuracy in the measurement can be greatly enhanced.

(2) since the acceleration acting on the hammer can be simply calculated, when the tester is tilted from the vertical line, the acceleration acting on the hammer can be compensated for and the accuracy in the measurement can be greatly enhanced.

DESCRIPTION OF THE PREFERRED EMBODIMENT

Figure 1:
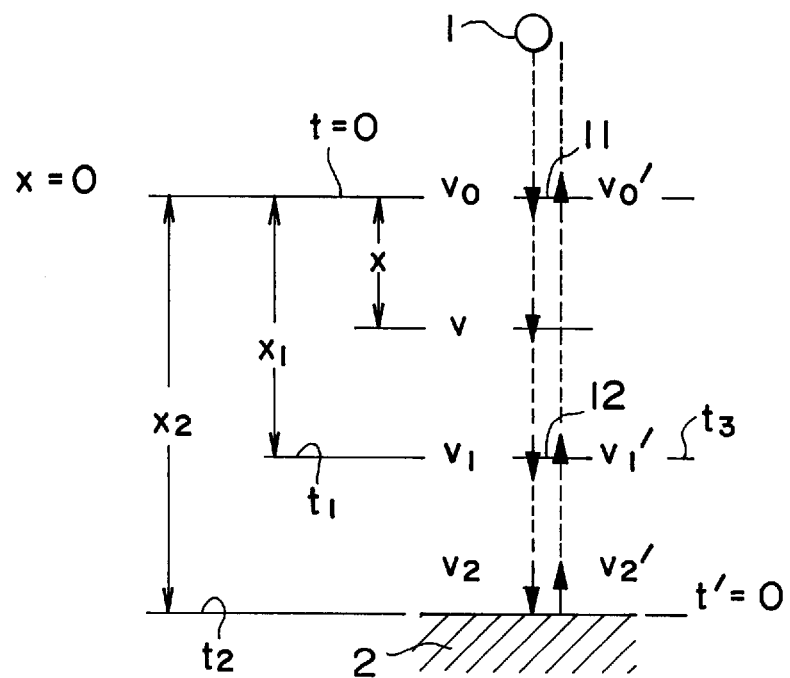
FIG. 1 is a schematic diagram showing the principle of a method as an embodiment of the invention of testing hardness in a rebound type hardness tester.
Figure 2:
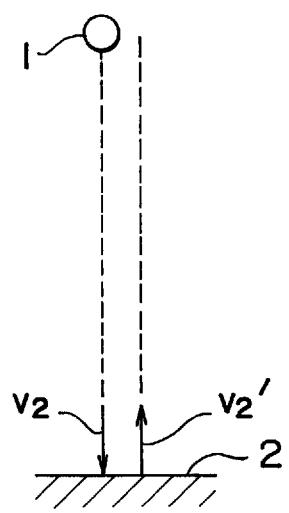
FIG. 2 is a schematic diagram showing the principle of a conventional method of testing hardness in a rebound type hardness tester.

A method as an embodiment of the present invention of testing hardness in a rebound type hardness tester will be described with reference to the accompanying drawing. FIG. 1 is a schematic diagram showing the principle of the method.

Refering to FIG. 1, reference numeral 11 denotes a first hammer velocity measurement point (hereinafter referred to as "first measurement point") and reference numeral 12 denotes a second hammer velocity measurement point (hereinafter referred to as "second measurement point").

Now it is set that the second measurement point 12 is located a distance $x_1$ below the first measurement point 11, the specimen 2 is located below the second measurement point 12, and the distance between the first measurement point 11 and the specimen 2 is $x_2$.

If, it is set that $v_0$: the velocity of the hammer 1 in the impacting course at the first measurement point 11, v: the velocity of the hammer 1 in the impacting course when t sec. elapsed, and $v_1$: the velocity of the hammer 1 in the impacting course at the second measurement point 12, and the acceleration applied to the hammer 1 is denoted by $\alpha$, then the following Equation 6 holds true.

$$v = \alpha t + v_0 \qquad \text{[Eq. 6]}$$

Hence, the displacement x of the hammer 1 when t sec. elapsed is given by Equation 7.

$$X = \int \frac{dv}{dt} = \frac{\alpha t^2}{2} + v_0 t + c \qquad \text{[Eq. 7]}$$

Since x=0 when t=0, c=0, and accordingly Equation 7 becomes Equation 8.

$$x = \frac{\alpha t^2}{2} + v_0 t \qquad \text{[Eq. 8]}$$

If, now, the time during which the hammer 1 makes a downward displacement of $x_1$ (then, the velocity of the hammer 1 is $v_1$) is denoted by $t_1$, Equations 6 and 8 become Equations 9 and 10, respectively.

$$t_1 = \frac{v_1 - v_0}{\alpha} \qquad \text{[Eq. 9]}$$

$$x_1 = \frac{\alpha t_1^2}{2} + v_0 t_1 \qquad \text{[Eq. 10]}$$

By substituting Equation 9 into Equation 10, the following Equation 11 is obtained.

$$x_1 = \frac{(v_1 - v_0)^2}{2\alpha} + \frac{v_0(v_1 - v_0)}{\alpha} = \frac{(v_1 - v_0) \times \{(v_1 - v_0) + 2v_0\}}{2\alpha} \qquad \text{[Eq. 11]}$$

$$= \frac{v_1^2 - v_0^2}{2\alpha}$$

Accordingly, the acceleration $\alpha$ is expressed as Equation 12.

$$\alpha = \frac{v_1^2 - v_0^2}{2 x_1} \qquad \text{[Eq. 12]}$$

Here, $x_1$, $v_1$, and $v_0$ are all known or actually measured values.

Next, the velocity $v_2$ of the hammer 1 when it impacts against the specimen 2 will be calculated with reference to FIG. 1.

If the time when the hammer 1 impacts against the specimen 2 (where x=$x_2$) is denoted by $t_2$ and the velocity at this time (impacting velocity) is denoted by $v_2$, then Equation 13 is derived from Equation 6 and Equation 14 is derived from Equation 8.

$$v_2 = \alpha t_2 + v_0 \qquad \text{[Eq. 13]}$$

$$x_2 = \frac{\alpha t_2^2}{2} + v_0 t_2 \qquad \text{[Eq. 14]}$$

By transforming Equation 14, we obtain Equation 15.

$$t_2 = \frac{-v_0 \pm \sqrt{v_0^2 + 2\alpha x_2}}{\alpha} \qquad \text{[Eq. 15]}$$

By substituting Equation 13 into Equation 15, we obtain Equation 16.

$$v_2 = \pm\sqrt{v_0^2 + 2\alpha x_2} \qquad \text{[Eq. 16]}$$

$$= \pm\sqrt{v_1^2 + 2\alpha(x_2 - x_1)}$$

Here, $V_0^2 + 2\alpha x_2 < 0$ has an imaginary root and represents a state in which the hammer is unable to reach the specimen because of a negative acceleration and, hence, such a state need not be considered. Further, positiveness and negativeness of Equation 16 is related with a parabolic movement in a constant-acceleration motion and, in the present instance, only the case of positiveness should be considered. By substituting Equation 12 into Equation 16, we obtain Equation 17.

$$v_2 = \sqrt{\frac{v_0^2(x_1 - x_2) + v_1^2 x_2}{x_1}} \qquad \text{[Eq. 17]}$$

Further, the velocity $v_2'$ of the hammer immediately after it rebounded from (the face of) the specimen 2 (where x=$x_2$) will be calculated.

If we denote the velocity of the hammer 1 when it has reached the second measurement point 12 after rebounding from the specimen 2 by v1', set the time t' at the moment the hammer 1 just rebounded at 0, and set the time when it has reached the second measurement point 12 at t'=$t_3$, and, further, set $x_2 - x_1 = -x_3$ (x becomes negative because the direction of the movement after the rebounding is reversed), then the following Equation 18 and Equation 19 hold true.

$$v_1' = \alpha t_3 - v_2' \qquad \text{[Eq. 18]}$$

$$x_3 = \frac{\alpha t_3^2}{2} - v_2' t_3 \qquad \text{[Eq. 19]}$$

From Equation 19, we obtain Equation 20.

$$t_3 = \frac{v_2'^2 \pm \sqrt{v_2'^2 + 2\alpha x_3}}{\alpha} \qquad \text{[Eq. 20]}$$

By substituting Equation 20 into Equation 18, we obtain Equation 21.

$$v_2' = \pm\sqrt{v_1'^2 + 2\alpha x_3} \qquad \text{[Eq. 21]}$$

Since the hardness H is defined by Equation 3, the hardness H can be calculated, from Equation 16 and Equation 21, by Equation 22.

$$H = k \times \sqrt{\frac{v_1'^2 + 2\alpha(x_2 - x_1)}{v_1^2 + 2\alpha(x_2 - x_1)}} \qquad \text{[Eq. 22]}$$

By using Equation 22, measurement of hardness of a specimen in a rebound type hardness tester can be performed without measuring the hammer velocity $v_2$ immediately before impacting and the hammer velocity $v_2'$ immediately after impacting which are difficult to measure.

At this time, the acceleration a can be calculated according to Equation 12 on the basis of the hammer velocities $v_1$ and $v_0$ (measured values) at the first measurement point 11 and the second measurement point 12 and the distance $x_1$ (measured value) between the first measurement point 11 and the second measurement point 12.

Incidentally, when the hammer 1 vertically drops, the acceleration α is known to be equal to the gravitational acceleration without using Equation 12.

Further, when the tester is tilted from the vertical line, the acceleration can also be calculated by compensating the gravitational acceleration for the tilt angle.

Examples of actual measurement will be shown below.

Actual Measurement Example 1

By setting $x_1=25$ mm and $x_2=35$ mm, when the actually measured values were $v_0=0.5$ m/s, $v_1=0.52$ m/s, and $v_1'=0.3$ m/sec, the acceleration is given, according to Equation 12, by Equation 23.

$$\alpha = \frac{0.52^2 - 0.5^2}{2 \times 0.025} = 0.408 \text{ m/s} \qquad \text{[Eq. 23]}$$

Accordingly, as the ratio between the velocities immediately before and after rebounding, Equation 24 is obtained from Equation 22.

$$\sqrt{\frac{0.3^2 + 2 \times 0.408 \times (0.035 - 0.025)}{0.52^2 \times 2 \times 0.408 \times (0.035 - 0.025)}} = 0.5936 \qquad \text{[Eq. 24]}$$

According to the conventional method of calculation using approximate values of $v_1$ and $v_1'$, the ratio between the velocities $v_1'/v_1$ becomes 0.5769, which is known to have an error of 2.89% as compared with the case of the present embodiment.

Actual Measurement Example 2

When the tester is oriented in an angle of depression of 45°, the acceleration α of the hammer is expressed as $$\alpha = g/\sin\theta = 9.80665 \div \sqrt{2} = 6.9343 \text{ m/s}^2. \qquad \text{[Eq. 25]}$$

When the actually measured values were $v_1=0.52$ m/s and $v_1'=0.3$ m/s the same as in the above actual measurement example 1, Equation 26 is obtained from Equation 22 as the ratio between the velocities immediately before and after rebounding.

$$\sqrt{\frac{0.3^2 + 2 \times 6.9343 \times 0.01}{0.52^2 + 2 \times 6.9343 \times 0.01}} = 0.7477 \qquad \text{[Eq. 26]}$$

In the case of this example, the error occurring in the conventional calculation method is 29.6%.

What is claimed is:

1. A method of measuring hardness in a rebound type hardness tester in which a hammer is caused to impact a specimen and a hardness test of said specimen is performed in accordance with the ratio of the velocities of the hammer before and after the impaction, said method of measuring hardness in a rebound type hardness tester comprising the step of calculating the hardness H of said specimen according to Equation 1 on the basis of a velocity $v_1$ in the impacting course and a velocity $v_1'$ in the rebounding course of said hammer at a second hammer velocity measurement point a distance $x_1$ closer to said specimen than a first hammer velocity measurement point, which is a distance $x_2$ apart from said specimen, along the passage for said hammer to go forward and backward, and said distance $x_1$, $$H = k \times \sqrt{\frac{v_1'^2 + 2\alpha(x_2 - x_1)}{v_1^2 + 2\alpha(x_2 - x_1)}} \qquad \text{[Eq. 1]}$$

where α denotes the acceleration acting on said hammer.

2. A method of measuring hardness in a rebound type hardness tester according to claim 1, wherein the acceleration α acting on said hammer is calculated according to Equation 2 on the basis of a velocity $v_0$ of said hammer in the impacting course at said first hammer velocity measurement point, a velocity $v_1$ of said hammer in the impacting course at said second hammer velocity measurement point, and said distance $x_1$, $$\alpha = \frac{v_1^2 - v_0^2}{2x_1} \qquad \text{[Eq. 2]}$$

* * * * *